United States Patent [19]

Dockner et al.

[11] Patent Number: 4,617,395

[45] Date of Patent: Oct. 14, 1986

[54] PREPARATION OF QUINOLINES

[75] Inventors: Toni Dockner, Meckenheim; Helmut Hagen, Frankenthal; Herbert Krug, Ludwigshafen, all of Fed. Rep. of Germany

[73] Assignee: BASF Aktiengesellschaft, Ludwigshafen, Fed. Rep. of Germany

[21] Appl. No.: 660,956

[22] Filed: Oct. 15, 1984

[30] Foreign Application Priority Data

Oct. 15, 1983 [DE] Fed. Rep. of Germany ....... 3337569

[51] Int. Cl.⁴ ................. C07D 215/02; C07D 215/12; C07D 215/18; C07D 215/20
[52] U.S. Cl. .................................... 546/178; 546/181; 546/180; 546/176; 546/171; 546/89; 546/84; 546/83; 546/82; 546/81; 546/80; 546/165; 546/166
[58] Field of Search ................ 546/180, 166, 178, 181

[56] References Cited

U.S. PATENT DOCUMENTS 2,451,610 10/1948 Campbell .......................... 546/181
3,899,492 8/1975 Povarov .............................. 596/178

FOREIGN PATENT DOCUMENTS 1075223 7/1967 United Kingdom .

OTHER PUBLICATIONS

Organikum, p. 629, R. H. E. Manske and M. Kulka, Org. Reactions 7, (1953), 59–98.

Primary Examiner—Glennon H. Hollrah
Assistant Examiner—D. B. Springer
Attorney, Agent, or Firm—Keil & Weinkauf

[57] ABSTRACT

Quinoline and substituted quinolines are prepared by reacting aniline or a substituted aniline with an α, β-monounsaturated aldehyde in a high-boiling mineral oil by a method in which the high-boiling mineral oil is replaced when it becomes enriched with by-products, and the said mineral oil enriched with by-products is removed.

4 Claims, 1 Drawing Figure

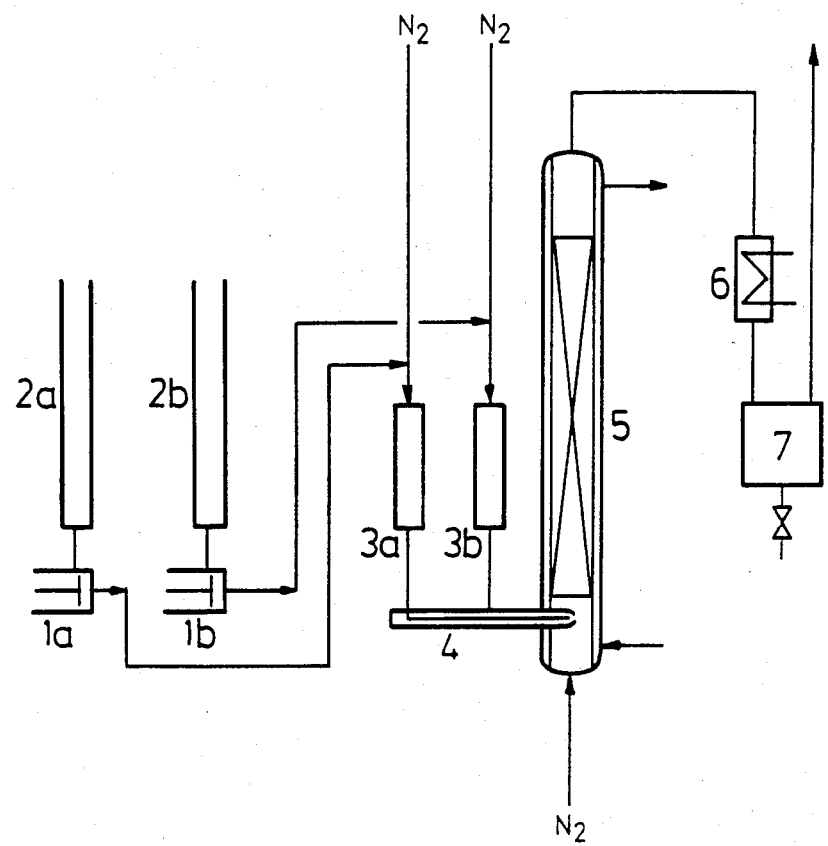

PREPARATION OF QUINOLINES

The present invention relates to a process for the preparation of quinolines by reacting an aromatic amine with unsubstituted or substituted acrolein at elevated temperatures, in a mineral oil.

Quinolines are prepared by the Skraup method, from unsubstituted or substituted aniline and glycerol (Organikum, page 561, R. H. E. Manske and M. Kulka, Org. Reactions 7, (1953), 59–98).

The method has a number of disadvantages and does not meet present-day energy and environmental requirements.

1. 3 moles of glycerol are required per mole of aniline.
2. One part of aniline requires from 2 to 3 parts of concentrated sulfuric acid, which is neutralized with alkali solution after the reaction. The salt solution to be disposed of still contains a very large amount of organic carbon.
3. The quinolines are obtained by an energy-consumptive steam distillation procedure, which is followed by solvent extraction. The aqueous raffinate contains solvents and residual product, which have to be disposed of.
4. The oxidation of the dihydroquinoline intermediate is carried out with nitrobenzene, arsenic pentoxide or iron(III) chloride.

The Doebner-Miller synthesis uses acrolein instead of glycerol, but has the other disadvantages of the Skraup synthesis.

It is an object of the present invention to provide a process for the preparation of quinolines which does not have the stated disadvantages and permits the by-products to be separated off in a simple manner.

We have found that this object is achieved, in accordance with the invention, if unsubstituted or substituted aniline is reacted with acrolein or another $\alpha,\beta$-unsaturated aldehyde at elevated temperatures, in a high-boiling mineral oil. In this procedure, only catalytic amounts of acid are required.

High-boiling mineral oils are high-boiling hydrocarbon fractions. ie. as a rule, refinery products having a boiling point of 150° C., such as gas oil, vacuum gas oil, heavy fuel oil, technical white oil, molten paraffin wax or an aromatic hydrocarbon oil. It is advantageous to use vacuum gas oil having a boiling point of above 200° C., in particular from 350° to 500° C.

The reaction of p-toluidine with methacrolein to give 3,6-dimethylquinoline can be represented by the following equation:

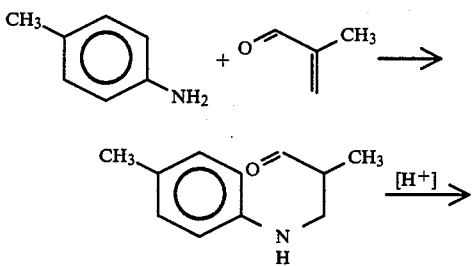

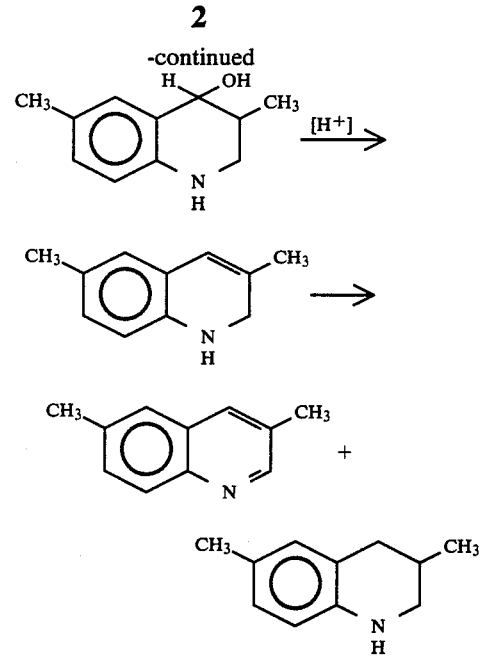

It is surprising that this multi-stage reaction takes place with good yields in a mineral oil at a temperature which is not excessively high, in the presence of only catalytic amounts of acid. The principal product is the desired quinoline or quinoline derivative. The tetrahydro derivative is obtained in amounts of only from 10 to 20%, based on the aniline employed, and can subsequently be converted to the desired product in a simple manner, by dehydrogenation by conventional methods.

In general, quinolines of the formula

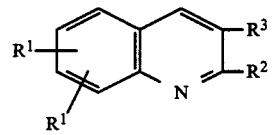

where the individual radicals $R^1$, $R^2$ and $R^3$ can be identical or different and are each hydrogen or an aliphatic radical, and the radicals $R^1$ may furthermore each be halogen, alkoxy, amino, monoalkylamino or dialkylamino, or, together with two adjacent carbon atoms, may form an isoxazole, oxazole, thiazole, isothiazole, furan, thiophene, pyrrole, imidazole or pyrazole radical, are prepared by reacting an aromatic amine of the formula

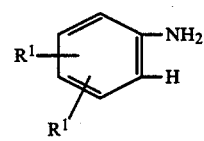

where $R^1$ has the above meanings, with an acrolein or one of its acetals of the formula

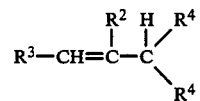

where $R^2$ and $R^3$ have the above meanings, and the individual radicals $R^4$ can be identical or different and are each alkoxy or together are an oxygen atom. The starting materials II and III can be reacted in stoichiometric amounts, or either component can be used in excess; advantageously, from 0.8 to 4, in particular from 1 to 2, moles of starting material III are employed per mole of starting material II. If starting materials II which carry 2 or 3 amino groups in the molecule are used, as a rule not more than 1.5, expediently from 0.8 to 1.5, advantageously from 1 to 1.5, in particular from 1.1 to 1.3, moles of starting material III are employed per mole of starting material II. If more than 1.5 moles of starting material III are employed per mole of starting material II, phenanthrolines or the corresponding triaza compounds containing 4 rings in the molecule are formed in increasing amounts when larger amounts of starting material III are used. Preferred starting materials II and III, and accordingly preferred end products ducts I, are those of the formulae where the individual radicals $R^1$, $R^2$ and $R^3$ can be identical or different and are each hydrogen, carboxyl or alkyl of 1 to 8, in particular 1 to 4, carbon atoms, and the radicals $R^1$ may furthermore each be fluorine, chlorine, bromine, amino, alkoxy, acylamino, or monoalkyl- or dialkylamino where each alkyl is of 1 to 8, in particular 1 to 4, carbon atoms, or the radicals $R^1$ together with two adjacent carbon atoms form an isoxazole, oxazole, thiazole, isothiazole, furan, thiophene, pyrrole, imidazole or pyrazole radical, and the individual radicals $R^4$ can be identical or different and are each alkoxy of 1 to 4 carbon atoms, or together are an oxygen atom. The above radicals can be further substituted by groups or atoms which are inert under the reaction conditions, eg. chlorine, bromine, alkyl or alkoxy, each of 1 to 4 carbon atoms, nitro or acylamino.

Examples of suitable starting materials II are aniline and o-methyl-, o-ethyl-, o-propyl-, o-isopropyl-, o-butyl-, o-isobutyl-, o-sec.-butyl-, o-tert.-butyl-, o-methoxy-, o-ethoxy-, o-propoxy-, o-isopropoxy-, o-butoxy-, o-isobutoxy-, o-sec.-butoxy-, o-tert.-butoxy-, o-dimethylamino-, o-diethylamino-, o-dipropylamino-, o-dibutylamino-, o-diisobutylamino-, o-di-sec.-butylamino-, o-di-tert.-butylamino-, o-N-methyl-N-ethylamino-, o-chloro-, o-bromo- and o-carboxyaniline; anilines which, instead of the above dialkylamino groups, are substituted by the corresponding monoalkylamino groups or by unsubstituted amino; anilines which are meta-substituted or para-substituted by the above groups; anilines which are disubstituted in the 2,4-, 2,3-, 2,5-, 3,4- or 3,5-position by identical or different groups from amongst those stated above; and thionaphthene, indole, benzoxazole, benzopyrazole, benzimidazole, benzisoxazole, benzothiazole, benzisothiazole or benzofuran which is substituted in the 4-, 5-, 6- or 7-position by amino.

Examples of suitable starting materials III are acrolein which is unsubstituted or substituted in the 2-position and/or 3-position by identical or different substituents from the group consisting of methyl, ethyl, propyl, isopropyl, butyl, isobutyl, sec.-butyl and tert.-butyl; and the dimethyl-, diethyl-, dipropyl- and diisopropyl-, dibutyl-, diisobutyl-, di-sec.-butyl-, di-tert.- butyl acetals of the above acroleins. Preferred reactive $\alpha,\beta$-unsaturated aldehydes are acrolein, methacrolein, crotonaldehyde, cinnamaldehyde and ethylacrolein.

The reaction according to the invention is preferably carried out using an acidic catalyst.

The catalysts used can be either insoluble or soluble in the mineral oil, and are accordingly dissolved, emulsified or suspended in the mineral oil. The reaction is carried out in general in the presence of an inorganic or organic acid, as a rule a catalytic amount, advantageously from 0.001 to 0.4, in particular from 0.005 to 0.05, equivalent, of acid being employed per mole of starting material II. Instead of monobasic acids, it is also possible to use equivalent amounts of polybasic acids. Examples of suitable acids are sulfonic acids, such as benzenesulfonic, p-toluenesulfonic and dodecylbenzenesulfonic acid, aliphatic carboxylic acids, such as oxalic acid, formic acid, acetic acid, propionic acid, caproic acid, capric acid, 3,5,5-trimethylhexanoic acid, lauric acid, palmitic acid, stearic acid, 2-ethylhexanecarboxylic acid, 2-ethylbutyric acid, 2-methylbutanoic acid, glycolic acid, lactic acid, pyruvic acid, tartaric acid, caprylic acid, trimethylacetic acid, succinic acid, isovaleric acid, valeric acid, glutaric acid and adipic acid, cycloaliphatic, araliphatic and aromatic carboxylic acids, such as benzoic acid, 2,3-, 2,4-, 2,5- and 2,6-dimethylbenzoic acid, mellitic acid, phenylpropionic acid, o-, m- and p-chlorobenzoic acid, cyclohexanecarboxylic acid, cyclopentanecarboxylic acid, phenylacetic acid, $\alpha$- or $\beta$-naphthoic acid, phthalic acid, o-, m- and p-toluic acid, isophthalic acid and terephthalic acid, acidic ion exchangers and mixtures of these. Toluenesulfonic acids, benzenesulfonic acid, dodecylbenzenesulfonic acid, sulfuric acid, sulfuric acid half esters, such as alkylsulfuric acid, phosphoric acid and its partially esterified derivatives, and boric acid and its acidic derivatives are preferred. It is also possible to use anhydrides, such as phosphorus pentoxide, sulfur dioxide or boron oxide. If the starting materials, in particular starting material II, contain carboxyl groups, ie. are themselves acids, an additional acid need not be used, the starting material also being employed as the catalyst. In such cases, it is expedient to use from 0.8 to 4, advantageously from 1 to 2, moles of starting material III per mole of starting material II.

The catalysts which are soluble in the mineral oil are added to the latter in general in amounts of from 0.01 to 25, preferably from 0.1 to 20, in particular from 1 to 7, % by weight, based on the mineral oil.

The quinoline synthesis is carried out in general at from 50° to 350° C., preferably from 80° to 250° C., in particular from 100° to 200° C.

Examples of suitable reactors are stirred kettles, but the novel process is advantageously carried out using vertical cylindrical reactors, such as bubble tray columns, bubble columns or packed columns. The starting material or materials are as a rule introduced in gaseous or liquid form at the base of the reactor filled with mineral oil. It may be advantageous to dilute the vaporized starting material with an inert gas, examples of suitable inert gases being steam, carbon dioxide and, preferably, nitrogen.

The reaction products are taken off in gaseous form at the top of the reactor and, advantageously, are then condensed. The condensation can also be followed by a purification stage, for example a distillation or fractionation.

The novel process can be carried out batchwise or continuously, the latter method being preferred. In the continuous procedure, it may be advantageous to introduce fresh mineral oil continuously and remove the spent solvent constantly, for example when the reaction is one in which crack products and polymers are formed; in this manner, the crack products are continuously removed from the reactor, together with the mineral oil.

In an equally preferred embodiment, the reactants are fed simultaneously and gradually into the catalyst-containing mineral oil, without the reaction products being removed continuously. When the mixture has become enriched with the end products, the feed of the starting materials is discontinued, and the useful products are separated from the mineral oil by distillation. High boiling by-products remain in the oil. The major part of the oil can be re-used, but some of it has to be removed.

As a rule, it is not economical to work up and recycle the mineral oil removed, since the mineral oil is in general available cheaply, for example in the form of fuel oil or vacuum gas oil. Advantageously, therefore, the mineral oil removed, which contains crack products, is fed for combustion, and fresh mineral oil is introduced into the reactor.

The novel process has the following substantial advantages over the prior art processes:

Catalytic amounts of acids are adequate, and the neutralization of large amounts of sulfuric acid is dispensed with. Polymers and condensates which are unavoidable in reactions of aldehydes with amines remain in the mineral oil; the latter need not be regenerated and, if desired after the catalyst has been separated off, is advantageously fed for combustion in a power station. Moreover, the process is substantially more economical both in its technical implementation and in its energy consumption. Finally, combustion of the reaction medium and of the byproducts present therein results in less environmental pollution.

EXAMPLE 1

In the apparatus shown in FIG. 1, 123 g/hour of acroline and 283 g/hour of 3-chloro-2-methylaniline were fed from the vessels 2a and 2b, by means of metering pumps 1a and 1b, into pre-evaporators 3a and 3b, and were vaporized therein together with, in each case, 30 liters/hour of $N_2$ at 170° C., and the vapor was then introduced into the reactor 5 via a two-material nozzle 4. The reaction temperature was 150° C.

The reactor consisted of a double-walled tube which was 1.25 m long and had a diameter of 65 mm. A perforated plate with 5 mm holes was located 3 cm above the nozzle entrance. The upper part of the reactor was filled with 3 liters of 5×5 mm glass rings.

The reactor contained 1.2 kg of vacuum gas oil of boiling point >350° C., with 5% by weight of dodecylbenzenesulfonic acid as a catalyst.

The resulting water of reaction and unreacted acrolein were condensed in a condenser 6, and collected in a collecting vessel 7. The 7-chloro-8-methylquinoline formed was recovered from the vacuum gas oil in the reactor by fractional distillation.

Based on the starting materials fed in per hour, 192 g of distillate (bp. 119° C./2 mm Hg) were obtained which, according to gas chromatography, contained 98% by weight of 7-chloro-8-methylquinoline, ie. 53%, based on 3-chloro-2-methylaniline employed.

A further fraction contained 82.6 g of 7-chloro-8-methyltetrahydroquinoline, and this could be converted to 7-chloro-8-methylquinoline by heating with 2-chloro-5-nitrotoluene. This increased the yield to 76%, based on 3-chloro-2-methylaniline employed.

EXAMPLE 2

The procedure described in Example 1 was followed, except that 1.2 kg of vacuum gas oil of boiling point 350° C. were employed, together with 1% by weight of dodecylbenzenesulfonic acid as a catalyst. Based on the starting materials fed in per hour, 210 g of distillate were obtained at a boiling point of 119° C./2 mm Hg; this distillate contained 98% by weight of 7-chloro-8-methylquinoline, corresponding to a yield of 58%, based on 3-chloro-2-methyl aniline employed.

A further fraction contained 36 g of 7-chloro-8-methyltetrahydroquinoline, and this could be oxidized to 7-chloro-8-methylquinoline by heating with 2-chloro-5-nitrotoluene. This increased the yield at 68%, based on 3-chloro-2-methylaniline employed.

EXAMPLE 3

The procedure described in Example 1 was followed, except that 187 g/hour of ethylacrolein and 283 g/hour of 3-chloro-2-methylaniline were employed. Distillation gave 335 g of distillate at a boiling point of 125° C./2 mm Hg. This distillate contained 75% by weight of 3-ethyl-7-chloro-8-methylquinoline and 22% by weight of 3-ethyl-7-chloro-8-methyltetrahydroquinoline, corresponding to a quinoline yield of 60%, based on 3-chloro-2-methylaniline employed.

The tetrahydro compound could likewise be converted to 3-ethyl-7-chloro-8-methylquinoline by oxidation with 2-chloro-6-nitrotoluene. This increased the yield to 77.5%.

EXAMPLE 4

The procedure described in Example 1 was followed, except that 123 g/hour of acrolein and 214 g/hour of 3-methylaniline were employed. Distillation gave 140 g of distillate of boiling point 128° C./15 mm hg. This distillate contained 92% by weight of 8-methylquinoline, corresponding to a yield of 45%, based on 3-methylaniline employed.

EXAMPLE 5

The procedure described in Example 1 was followed, except that 107 g/hour of 4-toluidine and 84 g/hour of methacrolein were employed. The product was distilled off under 5 mbar until the bottom temperature reached 250° C., and 110 g (70% of theory) of 3,6-dimethylquinoline of melting point 50° C. were obtained by crystallization with xylene.

EXAMPLE 6

The procedure described in Example 1 was followed, except that 130 g/hour of 2-chloroaniline and 84 g/hour of crotonaldehyde were employed. Distillation from the oil bed under 5 mbar until the bottom temperature reached 250° C., and crystallization of the distillate with xylene, gave 101 g (57% of theory) of 8-chloro-2-methylquinoline of melting point 64° C.

We claim:

1. In a process for the preparation of quinoline or a substituted quinoline by reacting aniline or a substituent aniline with an α,β-mono-unsaturated aldehyde or an acetal thereof in the presence of an acid, the improvement which comprises: reacting the aniline with the unsaturated aldehyde or acetal thereof at a temperature of from 80° to 250° C. in the presence of a mineral oil having a boiling point above 150° C., said mineral oil being selected from the group consisting of gas oil, vacuum gas oil, heavy fuel oil, technical white oil, molten paraffin wax and an aromatic hydrocarbon oil, said reaction further taking place in the presence of from 0.1 to 20% by weight of an organic acid catalyst based on the weight of the mineral oil.

2. The process of claim 1, wherein the acid catalyst is an organic acid that is soluble in the mineral oil.

3. The process of claim 1, wherein the quinoline or substituted quinoline and the corresponding tetrahydroquinoline formed in the reaction are continuously recovered in a first stage by fractional distillation and are passed to a second stage wherein the tetrahydroquinoline or substituted tetrahydroquinoline is oxidized to quinoline or substituted quinoline.

4. The process of claim 3, wherein in the first stage a portion of the mineral oil enriched with byproducts is continuously withdrawn as a sidestream from the reaction mixture and fresh mineral oil is added to the reaction mixture.

* * * * *